US012577551B2

(12) United States Patent (10) Patent No.: US 12,577,551 B2
Kim et al. (45) Date of Patent: Mar. 17, 2026

(54) METHOD OF PURIFYING BOTULINUM TOXIN

(71) Applicant: JETEMA CO., LTD., Gangwon-do (KR)

(72) Inventors: Jae Young Kim, Seoul (KR); Jeong Sun Nam, Seoul (KR); Seungho Kim, Seoul (KR); Seung Kwan Choi, Gyeonggi-do (KR); Hyun Taek Lim, Gyeonggi-do (KR); Jin Hee Choi, Seoul (KR)

(73) Assignee: JETEMA CO., LTD., Gangwon-Do (KR)

( * ) Notice: Subject to any disclaimer, the term of this patent is extended or adjusted under 35 U.S.C. 154(b) by 730 days.

(21) Appl. No.: 17/603,359

(22) PCT Filed: Apr. 14, 2020

(86) PCT No.: PCT/KR2020/005042
§ 371 (c)(1),
(2) Date: Oct. 13, 2021

(87) PCT Pub. No.: WO2020/213929
PCT Pub. Date: Oct. 22, 2020

(65) Prior Publication Data
US 2022/0204957 A1 Jun. 30, 2022

(30) Foreign Application Priority Data

Apr. 15, 2019 (KR) ........................ 10-2019-0043869

(51) Int. Cl.
*C12N 9/52* (2006.01)

(52) U.S. Cl.
CPC ........ *C12N 9/52* (2013.01); *C12Y 304/24069* (2013.01)

(58) Field of Classification Search
None
See application file for complete search history.

(56) References Cited

U.S. PATENT DOCUMENTS

| | | | |
|---|---|---|---|
| 7,354,740 B2 | 4/2008 | Xiang et al. |
| 7,452,697 B2 | 11/2008 | Luo et al. |
| 9,206,409 B2 | 12/2015 | Ton et al. |
| 2003/0008367 A1 | 1/2003 | Oguma |
| 2006/0228780 A1 | 10/2006 | Luo et al. |
| 2007/0037257 A1 | 2/2007 | Smith et al. |
| 2018/0117128 A1 | 5/2018 | Palan et al. |
| 2019/0100564 A1 | 4/2019 | Hackett et al. |

FOREIGN PATENT DOCUMENTS

| | | | |
|---|---|---|---|
| AU | 2010310749 B2 | 10/2010 |
| AU | 2012201519 A1 | 4/2012 |
| CN | 108350043 A | 7/2018 |
| EA | 201890851 A1 | 8/2018 |
| JP | 2011074025 A | 4/2011 |
| KR | 1020070116710 A | 12/2007 |
| KR | 1020180037420 A | 4/2008 |
| KR | 1020090120222 A | 11/2009 |
| KR | 1020120099431 A | 9/2012 |
| KR | 1021020105417 A | 9/2012 |
| RU | 2561459 C2 | 8/2015 |
| RU | 2627159 C2 | 8/2017 |
| WO | WO2006042542 A2 | 4/2006 |
| WO | 2006096164 A1 | 9/2006 |
| WO | WO2011008713 A1 | 1/2011 |
| WO | 2011050072 A1 | 4/2011 |
| WO | 2017055274 A1 | 4/2017 |
| WO | 2018200991 A1 | 11/2018 |

OTHER PUBLICATIONS

Russian Office Action Issued on Oct. 12, 2022 in counterpart Russian Patent Application No. 2021128382, Oct. 12, 2022.
Search Report Issued on Oct. 12, 2022 in counterpart Russian Patent Application No. 2021128382.
English Translation of Office Action issued on Mar. 20, 2024 for Chinese Patent Application 202080034458.2.
Search Report issued on Mar. 18, 2024 for the Chinese patent application 202080034458.2.
English Translation of Notice of Allowance issued in counterpart Korean Patent Application No. 10-2020-0044719, Mar. 23, 2023.
English Translation of Notice of Allowance issued in counterpart Russian Patent Application No. 2021128382, Mar. 2, 2023.
Johnson, S.K., et al., "Scale-up of the fermentation and purification of the recombinant heavy chain fragment C of botulinum neurotoxin serotype F, expressed in Pichia pastoris", Protein & Expression Purification, 2003, pp. 1-9, vol. 32, Publisher: Elsevier.
Kannan, K., et al., "Methods Development for the Biochemical Assessment of Neurobloc TM (Botulinum Toxin Type B)", Movement Disorders, 2000, pp. 18-26, vol. 15, No. 2, Publisher: Movement Disorders Society.
Schantz, E., et al., "Properties and Use of Botulinum Toxin and Other Microbial Neurotoxins in Medicine", Microbiological Reviewss, 1992, pp. 80-99, vol. 56, No. 1, Publisher: American Society for Microbiology.
Schmidt, J., et al., "Purification of Type E Botulinum Neurotoxin by High-Performance Ion Exchange Chromatography", Analytical Biochemistry, 1986, pp. 213-219, vol. 156.

(Continued)

*Primary Examiner* — Richard G Hutson
(74) *Attorney, Agent, or Firm* — HULTQUIST, PLLC; Steven J. Hultquist

(57) ABSTRACT

Disclosed is a method of purifying a botulinum toxin comprising (a) pre-treating a culture solution containing a botulinum toxin, (b) purifying the pre-treated botulinum toxin using cation exchange chromatography, (c) purifying the botulinum toxin using hydrophobic chromatography, and (d) purifying the botulinum toxin using anion exchange chromatography. The method is capable of purifying a botulinum toxin with high purity and activity and is thus useful for botulinum toxin production.

8 Claims, 7 Drawing Sheets

(56)     References Cited

OTHER PUBLICATIONS

Zhou, L., et al., "Expression and Purification of the Light Chain of Botulinum Neurotoxin A: A Single Mutation Abolishes Its Cleavage of SNAP-25 and Neurotoxicity after Reconstitution with the Heavy Chain", Biochemistry, 1995, pp. 15175-15181, vol. 34, Publisher: American Chemical Society.

EESR Issued in counterpart European Patent Application No. 20791857.4 on Jan. 9, 2023.

| | RT | Area | % Area | Height | K Prime | Resolution | Symmetry Factor | USP Plate Count |
|---|---|---|---|---|---|---|---|---|
| 1 | 8.862 | 1087372 | 95.53 | 25844 | 0.772 | | 1.198 | 1066 |
| 2 | 10.304 | 49923 | 4.47 | 2009 | 1.061 | 1.655 | | 3806 |

| | RT | Area | % Area | Height |
|---|---|---|---|---|
| 1 | 6.691 | 74989 | 3.66 | 2080 |
| 2 | 7.656 | 1932824 | 94.27 | 39254 |
| 3 | 9.350 | 20136 | 0.98 | 598 |
| 4 | 11.976 | 12441 | 0.61 | 325 |
| 5 | 13.776 | 9867 | 0.48 | 660 |

Purity : 99.37 %

|   | RT | Area | % Area | Height |
|---|---|---|---|---|
| 1 | 7.907 | 1913976 | 99.37 | 40181 |
| 2 | 9.584 | 10529 | 0.55 | 191 |
| 3 | 10.958 | 1565 | 0.08 | 57 |

METHOD OF PURIFYING BOTULINUM TOXIN

CROSS-REFERENCE TO RELATED APPLICATIONS

This is a United States national phase under 35 USC § 371 of International Patent Application No. PCT/KR20/05042 filed Apr. 14, 2020, which in turn claims priority under 35 USC § 119 of Korean Patent Application No. 10-2019-0043869 filed Apr. 15, 2019. The disclosures of all such applications are hereby incorporated herein by reference in their respective entireties, for all purposes.

BACKGROUND OF THE INVENTION

Field of the Invention

The present invention relates to a method for purifying a botulinum toxin, and more specifically to a purification method capable of obtaining a highly pure and active botulinum toxin through a simple process of cation exchange chromatography, hydrophobic chromatography and anion exchange chromatography.

Description of the Related Art

Botulinum toxin is a neurotoxic protein produced by bacteria such as *Clostridium butyricum, Clostridium baratii*, and *Clostridium botulinum*. Botulinum toxin blocks neuromuscular transmission and causes neuroparalytic diseases in humans and animals. In particular, botulinum toxin type A is known to be very fatal to humans. In addition to botulinum toxin type A, seven other botulinum toxins types, namely B, Cl, D, E, F, G and H, have been identified. Each botulinum toxin type is distinguished by a corresponding type-specific antibody, and there is a difference in the severity of the paralysis caused thereby and the animal species affected thereby.

The molecular weight of the botulinum toxin protein molecule is about 150 kDa, including a light chain of about kDa and a heavy chain of about 100 kDa conjugated thereto. However, botulinum toxin released from *Clostridium* bacteria is released in the form of a complex of a 150 kDa toxin protein with at least one non-toxin protein. For example, botulinum toxin is released as 900 kDa, 500 kDa and 300 kDa complexes.

Botulinum toxin may be very fatal to humans, but botulinum toxin has recently been developed to treat a variety of symptoms including neuromuscular disorders characterized by skeletal muscle hyperactivity. For example, Botox® is a trademark of botulinum toxin A commercially developed by Allergan, Inc., which is used to alleviate or treat blepharospasm, strabismus, cervical dystonia and *glabella* (facial) wrinkles, and research is underway to develop applications suitable for other serotypes and clinically utilize the serotypes.

Botulinum toxins for clinical use are generally isolated from cell cultures. In this case, a variety of purification methods are used.

For example, botulinum toxin is purified in a complexed form by a series of precipitation and tangential flow filtration steps [see Schantz E. J. et al., *Microbiol. Rev.* 1992 March 56 (1): 80-99]. However, this method typically provided a relatively low yield of less than about 10%. Other methods used include size exclusion, ion exchange and/or affinity chromatography [see, e.g., Schmidt J. J. et al., *Anal.*

*Biochem.* 156:213, 1986; Kannan K. et al., *Mov. Disord.* 2000; 15 (Suppl 2): 20 (2000); and US Patent No. 2003/0008367].

Another method is independent synthesis of one of the heavy or light chains of botulinum toxin by recombinant means, rather than a complete and biologically active botulinum toxin protein [see e.g., Zhou L. et al., *Biochemistry,* 34 (46): 15175, (1995); and Johnson S. K. et al., *Protein Expr. and Purif.;* 32: 1-9, (2003)]. However, these methods disadvantageously require an additional step of reforming a complete and biologically active botulinum toxin protein.

More recent methods involve the use of hydrophobic interaction chromatography, mixed-mode and/or ion exchange chromatography to purify botulinum toxins as complexes (see: U.S. Pat. Nos. 7,452,697 and 7,354,740].

However, there is still a need in the technical art for an improved purification method for isolating complete botulinum toxins that are stable and biologically active. Accordingly, as a result of extensive efforts to develop a purification method for isolating highly pure and active botulinum toxins in a simplified manner, the present inventors found that a highly pure and active botulinum toxin can be purified using a simple process of cation exchange chromatography, hydrophobic chromatography and anion exchange chromatography, and in particular, a botulinum toxin can be purified to a purity of 99% or more using an SP column as a cation exchange resin and using a phenyl column as a hydrophobic resin and using a Q column as a anion exchange resin. Based on this finding, the present invention has been completed.

PRIOR ART DOCUMENT

Patent Document

US Patent Laid-open No. 2003/0008367
U.S. Pat. No. 7,452,697
U.S. Pat. No. 7,354,740

Non-Patent Document

Schantz E J, et al, Properties and use of botulinum toxin and other microbial neurotoxins in medicine, Microbiol. Rev. 1992 March 56(1):80-99

Schmidt J. J., et al., Purification of type E botulinum neurotoxin by high-performance ion exchange chromatography, Anal. Biochem. 1986 July; 156(1):213-219

Kannan K. et al., Methods development for the biochemical assessment of NeuroBloc (botulinum toxin type B), Mov. Disord. 2000; 15(Suppl 2):20

Wang Y. C., The preparation and quality of botulinum toxin type A for injection (BTXA) and its clinical use, Dermatol. Las. Faci. Cosm. Surg. 2002; 58

Zhou L. et al., Expression and purification of the light chain of botulinum neurotoxin A: A single mutation abolishes its cleavage of SNAP-25 and neurotoxicity after reconstitution with the heavy chain, Biochemistry 1995; 34(46):15175-81

Johnson S. K., et al., Scale-up of the fermentation and purification of the recombination heavy-chain fragment C of botulinum neurotoxin serotype F expressed in *Pichia pastoris*, Protein Expr. and Purif. 2003; 32: 1-9

SUMMARY OF THE INVENTION

Therefore, the present invention has been made in view of the above problems, and it is an object of the present invention to provide a method for purifying a highly pure and active botulinum toxin using a simple process.

In accordance with an aspect of the present invention, the above and other objects can be accomplished by the provision of a method of purifying a botulinum toxin comprising (a) pre-treating a culture solution containing a botulinum toxin, (b) purifying the pre-treated botulinum toxin using cation exchange chromatography, (c) purifying the botulinum toxin using hydrophobic chromatography and (d) purifying the botulinum toxin using anion exchange chromatography.

Effects of the Invention

The present invention can improve the purity of a botulinum toxin after purification, and can maintain the activity thereof using only a simple process including cation exchange chromatography, hydrophobic chromatography and anion exchange chromatography, and is thus useful for botulinum toxin production.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
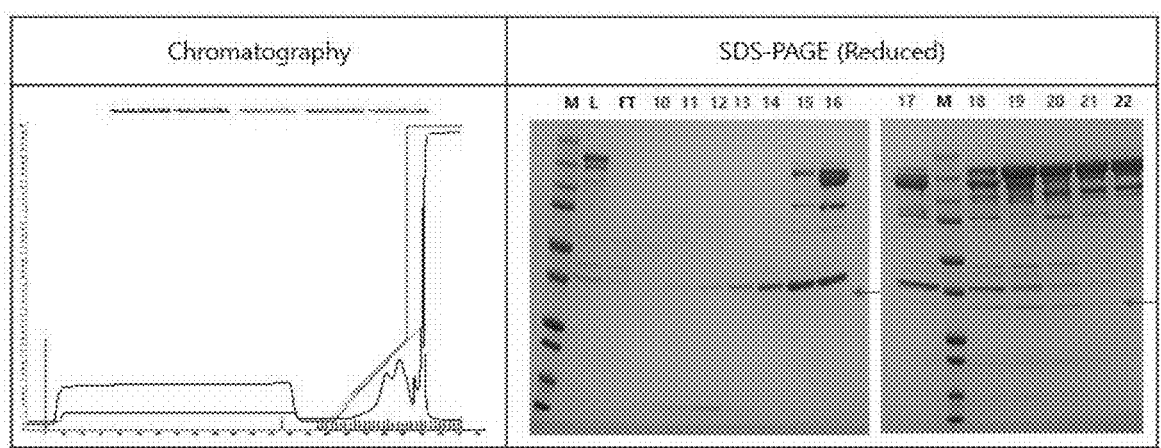
FIG. 1 shows the result of FPLC and SDS-PAGE analysis of a botulinum toxin in an eluent after cation exchange chromatography according to an embodiment of the present invention.

Unless defined otherwise, all technical and scientific terms used herein have the same meanings as appreciated by those skilled in the field to which the present invention pertains. In general, the nomenclature used herein is well-known in the art and is ordinarily used.

In the present invention, it was identified that, when a botulinum toxin culture solution is purified through a series of processes of cation exchange chromatography, hydrophobic chromatography and anion exchange chromatography, a highly pure and active botulinum toxin in a uniform form of about 900 kDa can be isolated and purified compared to a botulinum toxin prepared by a conventional method. In particular, it was identified that, when using an SP column as a cation exchange resin, using a phenyl column as a hydrophobic resin and using a Q column as an anion exchange resin, a botulinum toxin can be purified to a purity of 99% or more.

Accordingly, in one aspect, the present invention is directed to a method of purifying a botulinum toxin comprising (a) pre-treating a culture solution containing a botulinum toxin, (b) purifying the pre-treated botulinum toxin using cation exchange chromatography, (c) purifying the botulinum toxin using hydrophobic chromatography and (d) purifying the botulinum toxin using anion exchange chromatography.

In the present invention, the cation exchange resin is preferably a SP column, the hydrophobic chromatography resin is preferably a phenyl column and the anion exchange resin is preferably a Q column.

In the present invention, the SP column is a column filled with a material containing a sulfopropyl functional group, the phenyl column is a column packed with a material containing a phenyl group and the Q column is a column packed with a material containing a quaternary ammonium (Q) functional group.

The culture solution containing a botulinum toxin in step (a) of the present invention may be a culture solution of a *Clostridium botulinum* strain obtained using a conventional method known in the art, and may be obtained by culturing using a conventional medium used for culture, in particular, using a medium excluding an animal-derived component, preferably for example a PYG medium (containing potato peptone 3%, yeast extract 1% and glucose 1%).

The botulinum toxin-producing strain used in the present invention may be *Clostridium botulinum* or a variant thereof, and most preferably *Clostridium botulinum* type A, NCTC13319, but is not limited thereto. It will be apparent to those skilled in the art that any strain capable of producing a botulinum toxin can be used.

In a specific embodiment, the pre-treatment with the culture solution in step (a) of the present invention may be acid precipitation or ultrafiltration of the culture solution subjected to sterilization (by, for example, depth filtration and/or sterilization filtration), but is not limited thereto.

Acid precipitation may be precipitation using sulfuric acid or precipitation using hydrochloric acid, but is not limited thereto. That is, the acid precipitation in step (a) of the present invention may be acid precipitation of a culture solution containing a botulinum toxin using an acid such as sulfuric acid in one embodiment or hydrochloric acid in another embodiment, such that, after completion of the culture, the pH is adjusted to 3.0 to 4.5, preferably 3.3 to 4.0, and most preferably 3.4 to 3.6.

An ultrafiltration membrane may be a cassette type or a hollow fiber, but is not limited thereto. That is, in the step (a) of the present invention, the ultrafiltration may be ultrafiltration using a membrane with a size of 50 kDa to 500 kDa, preferably 100 kDa to 300 kDa, to collect a culture solution containing a botulinum toxin.

In addition, DNase, RNase, nuclease and/or Benzonase may be optionally used in order to remove nucleic acids during the pretreatment, but the invention is not limited thereto.

The present invention may include additional purification in order to increase the purity of the resultant botulinum toxin. The purification in the present invention is a step for additionally removing impurities from the acid precipitate, and may be carried out by a conventional process such as known microfiltration, ultrafiltration, precision filtration or depth filtration. In one embodiment of the present invention, microfiltration may be performed using 0.1 to 0.4 μm hollow fibers.

In step (b) of the present invention, the cation exchange chromatography includes binding, to a cation exchange chromatography column, the pre-treated botulinum toxin dissolved in a buffer having a suitable concentration and pH for the binding of the botulinum toxin to the column and then performing elution using a buffer solution having an increased salt concentration. In the cation exchange chromatography, a botulinum toxin having a non-complex form is removed.

In the method for purifying a botulinum toxin according to the present invention, the column used for cation exchange chromatography is preferably a column packed with a resin having a functional group selected from the group consisting of carboxymethyl (CM), sulfoethyl (SE), sulfopropyl (SP), phosphate (P) and sulfonate (S).

In the present invention, from the viewpoint of removing impurities and keeping the botulinum toxin highly active, the cation exchange chromatography may be carried out using an SP column, preferably an SP sepharose HP column, SP sepharose FF column, CAPTOR S column or the like, and more preferably an SP sepharose HP column, but is not limited thereto.

In the present invention, the SP sepharose HP column is a column packed with a resin that contains a sulfopropyl functional group, has a 6% spherical, cross-linked agarose matrix form, and has a DBC of 55 mg/mL based on ribonuclease A and a particle size of 34 μm.

The botulinum toxin in step (b) is dissolved in a 10 to 30 mM sodium citrate buffer having a pH of 4.5 to 5.3 and is then injected into the SP column.

The botulinum toxin in step (b) is eluted with a 10 to 30 mM sodium citrate buffer having a pH of 4.5 to 5.5 supplemented with 0.5 to 1.5M sodium chloride, but is not limited thereto.

In step (c) of the present invention, the hydrophobic chromatography includes binding, to a hydrophobic chromatography column, the solution containing a botulinum toxin eluted during the cation exchange chromatography in step (b) dissolved in a buffer having a suitable concentration and pH for the binding of the solution to the hydrophobic chromatography column, and then performing elution using a buffer solution having an decreased salt concentration. In the hydrophobic chromatography, a botulinum toxin having a non-complex form is further removed.

In the method for purifying a botulinum toxin according to the present invention, the column used for hydrophobic chromatography is a column filled with a resin having a functional group selected from the group consisting of ether, isopropyl, butyl, octyl and phenyl, but is not limited thereto.

In the present invention, in order to effectively separate the non-complex protein, the hydrophobic chromatography may be carried out using a phenyl column, preferably a phenyl sepharose HP column, a phenyl sepharose FF (Fast Flow) column, a CAPTOR phenyl column or the like, and more preferably, a phenyl sepharose HP column, but is not limited thereto.

The phenyl sepharose HP column used in the present invention is a column packed with a resin that has a highly cross-linked agarose 6% matrix form, and has a degree of substitution of 25 μmol phenyl groups/mL and a bead size of 34 um.

In step (c), the botulinum toxin may be dissolved in a 30 to 70 mM sodium phosphate buffer having a pH of 5.7 to 6.7 supplemented with 1.8 to 2.2M sodium chloride, and may then be injected into a phenyl column, but is not limited thereto.

In step (c), the botulinum toxin may be eluted with a 30 to 70 mM sodium phosphate buffer having a pH of 5.7 to 6.7, but is not limited thereto.

In the step (d) of the present invention, anion exchange chromatography includes binding, to an anion exchange chromatography column, the botulinum toxin eluted during hydrophobic chromatography dissolved in a buffer having a suitable concentration and pH for binding the botulinum toxin to the column, and then performing elution using a buffer solution having an increased salt concentration. In the anion exchange chromatography, other impurities are removed and the purity of botulinum toxin of 900 kDa is increased.

In the method for purifying botulinum toxin according to the present invention, the column used for the anion exchange chromatography is a column packed with a resin having a functional group selected from the group consisting of diethylaminoethyl (DEAE), quaternary aminoethyl (QAE) and quaternary ammonium (Q), but is not limited thereto.

In the present invention, in order to remove other impurities and particularly increase the purity of botulinum toxin of 900 kDa, the anion exchange chromatography may be carried out using a Q column, preferably a CAPTOR Q ImpRes column, Toyopearl Super Q 650M column, Q sepharose FF column, Q Sepharose High-Performance (Q Sepharose HP) column, or the like, and more preferably a CAPTOR Q ImpRes column.

The CAPTOR Q ImpRes column used in the present invention is a column packed with a resin that has a high-flow agarose matrix containing a quaternary ammonium (Q) functional group, a total ionic capacity of 0.15 to 0.18 mmol (Cl-)/mL, DBC of 55 mg/mL based on BSA and a bead size of 40 um.

The botulinum toxin in step (d) is dissolved in a 40 to 60 mM sodium phosphate buffer having a pH of 5.7 to 6.7 and then injected into the Q column, but is not limited thereto.

In step (d), the botulinum toxin may be eluted with a 40 to 60 mM sodium phosphate buffer having a pH of 5.7 to 6.7, supplemented with 0.8 to 1.2M sodium chloride, but is not limited thereto.

The botulinum toxin purified by the method described above may be a botulinum toxin type A having a purity of at least 99%, and the purified botulinum toxin may have a higher purity than a botulinum toxin purified by a conventional method.

The botulinum toxin may be derived from *Clostridium botulinum* type A, NCTC13319, but is not limited thereto.

As used herein, the term "fraction" refers to a group of passing-through substances containing at least one target molecule, which are each separated and collected by a separation method, wherein the at least one target molecule (such as a botulinum toxin) contained along with one or more impurities in a biopharmaceutical agent passes through a substance binding to the one or more impurities and the target molecule usually does not bind to the substance (i.e., flows through the substance), or binds thereto and is then eluted.

As used herein, the term "purification" refers to an operation of increasing the purity by removing co-existing impurities from a certain substance and in this specification, purification refers to isolation of a botulinum toxin produced when overgrown botulinum bacteria die, from a culture solution of botulinum bacteria, and means a process for improving a purity during a botulinum toxin production process.

EXAMPLE

Hereinafter, the present invention will be described in more detail with reference to examples. However, it will be obvious to those skilled in the art that these examples are provided only for illustration of the present invention and should not be construed as limiting the scope of the present invention.

Example 1. Preparation of Samples and Experimental Materials 1-1. Sample Preparation The botulinum strain used in the present invention was *Clostridium botulinum* type A, NCTC13319, and the strain was primarily inoculated into 500 mL PYG medium (potato peptone 3%, yeast extract 1%, glucose 1%) and cultured under anaerobic conditions at 34±1° C. in a ReadytoProcess WAVE 25 incubator for 12 hours to 24 hours. After culturing, when the growth of the strain reached the log phase, 100 mL of the strain was inoculated into 5 L PYG medium and cultured under anaerobic conditions in a ReadytoProcess WAVE 25 incubator for 40 to 72 hours. The culture solution was sterilized using a sterilizing filter, and only the culture solution was recovered. The culture solution was titrated to pH 3.5 using 3N sulfuric acid, precipitation was observed, and then the result was stored in a refrigerated state for 16 hours or more.

1-2. Preparation of Experimental Materials

The experimental materials used in the present invention were as follows: purified water (ultrapure water or water with quality equal to or higher than ultrapure water), butyl SEPHAROSE® HP high molecular weight gel (GE Healthcare, 175432), Q-SEPHAROSE®-HP high molecular weight gel (GE Healthcare, 171014), phenyl SEPHAR-OSE® HP high molecular weight gel (GE Healthcare, 171082), Q-SEPHAROSE®-FF high molecular weight gel (GE Healthcare, 170510), SP-SEPHAROSE®-FF high molecular weight gel (GE Healthcare, 170729), DEAE-FF (GE Healthcare, 170709), SP-SEPHAROSE®-HP high molecular weight gel (GE Healthcare, 171087), CAPTO® Q ImpRes chromatography medium (GE Healthcare, 175470), citric acid (Merck, 1.37002.5000), tri-sodium citrate dehydrate (Merck, 1.37042.5000), sodium phosphate monobasic (Merck, 1.06349.1000), sodium phosphate dibasic (Merck, 1.06585), and sodium chloride (Merck, 1.37017.5000).

Example 2. Purification of Botulinum Toxin 2-1. Microfiltration

Microfiltration equipment, AKTA flux 6 (GE Healthcare) was turned on and 0.2 μm hollow fibers were connected thereto. 5 L of distilled water was added thereto, and the equipment and hollow fibers were washed twice at TMP of 0.3. 5 L of the sulfuric acid precipitate of the botulinum toxin culture solution prepared in Example 1-1 was injected into the microfiltration equipment, and two steps of concentration to 1 L at TMP of 0.3, and further concentration from 3 L to 1 L after addition of 2 L of DW thereto, were repeated 5 times. 500 mL of 200 mM sodium citrate (pH 5.5) was added, and extraction was performed through circulation for 1 hour 30 minutes. The extract was recovered through a permeate line of the microfiltration equipment, and 300 kDa cut-off hollow fibers were connected to the microfiltration equipment. The extract was added thereto and concentrated to 500 mL at a TMP of 0.3 bar, recovered, and stored at 4° C.

2-2. Cation Exchange Chromatography

The SP-HP resin was packed in a HiScale 50/20 column (GE Healthcare, 28964445) to a height of 8 to 12 cm, and was then mounted in an AKTA Pure system. The column was equilibrated by flowing an equilibration/wash buffer (20 mM sodium citrate pH 4.8). The sample prepared in Example 2-1 was adjusted to pH 4.8 with 1M citric acid and diluted 5-fold in 2,000 mL of distilled water. The sample was injected into the column at 15 mL/min. After the injection, the column was washed with 380 mL of equilibration/wash buffer (20 mM sodium citrate, pH 4.8). After washing, the equilibration/elution buffer was injected in accordance with step 1) 5 CV, 30% gradient (linear gradient) and step 2) 3 CV, 100% gradient (step gradient), and 50 mL fractions were sequentially obtained (See Table 1). A total of 31 fractions were sequentially obtained, and each of the fractions was identified by SDS-PAGE.

TABLE 1

| Column Resin | SP Sepharose HP |
| --- | --- |
| Column Volume | 190 mL |
| Binding and Washing Buffer | 20 mM sodium citrate pH 4.8 |
| Elution Buffer | 20 mM sodium citrate/1M sodium chloride, pH 4.8 |

The results are shown in FIG. 1. HA33 was detected from Fractions 10 to 21 of the total of 31 fractions, and the botulinum toxin in the form of a 900-kDa complex was purified from the corresponding fractions.

2-3. Hydrophobic Chromatography

The phenyl-HP resin was packed in a HiScale 26/20 column (GE Healthcare, 28964514) to a height of 7 to 11 cm and then mounted in an AKTA Pure system. The column was equilibrated by flowing an equilibration/wash buffer (50 mM sodium phosphate, 2M sodium chloride, pH 6.2). A total of 600 mL of Fractions 10 to 21, eluted from the SP sepharose HP column of Example 2-2, was collected, and the pH was adjusted to 6.2 with a 1M sodium phosphate dibasic solution. The sample added with 600 mL of 50 mM sodium phosphate and 4 M sodium chloride at pH 6.2 was injected at 8 mL/min. After the injection, the column was washed with 94 mL of equilibration/washing buffer (50 mM sodium phosphate, 2M sodium chloride pH 6.2). After washing, the equilibration/elution buffer was injected in accordance with step 1) 10 CV, 100% gradient (linear gradient), and step 2) 3 CV, 100% gradient (step gradient), 23 mL of a total of 27 fractions were sequentially obtained, and each of the fractions was identified by SDS-PAGE.

TABLE 2

| Column Resin | Phenyl Sepharose HP |
| --- | --- |
| Column Volume | 47 mL |
| Binding and Washing Buffer | 50 mM sodium phosphate/2M sodium chloride, pH 6.2 |
| Elution Buffer | 50 mM sodium phosphate, pH 6.2 |

Figure 2:
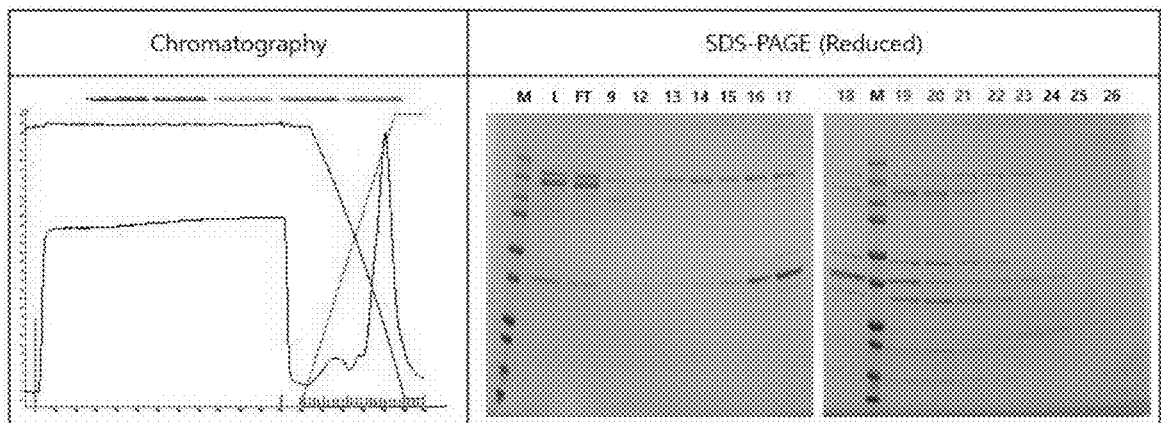
FIG. 2 shows the result of FPLC and SDS-PAGE analysis of a botulinum toxin in an eluent after hydrophobic chromatography according to an embodiment of the present invention.

The results are shown in FIG. 2, and a botulinum toxin as a 900-kDa complex was detected in Fractions 16 to 23 among the total of 27 fractions.

2-4. Anion Exchange Chromatography

The CAPTOR-Q ImpRes resin was packed in an Omnifit 6.6/25 column (Diba, 006EZ0625AA) to a height of 8 to 12 cm and then mounted in an AKTA Pure system. A total of 168 mL of Fractions 16 to 23 eluted from the phenyl sepharose HP column of Example 2-3 was subjected to diafiltration (DF) to 100 times with 50 mM sodium phosphate (pH 6.2) buffer using a dialysis membrane (Spectra/Por, 132680). The column was equilibrated by flowing an equilibration/washing buffer (50 mM sodium phosphate, pH 6.2). The sample prepared in Example 2-3 was injected at 1 mL/min. After the injection, the column was washed with 18 mL of equilibration/washing buffer (50 mM sodium phosphate, pH 6.2). After washing, an equilibration/elution buffer was injected in accordance with step 1) 2 CV, 15% step gradient, step 2) 2 CV, 20% step gradient, step 3) 2 CV, 30% step gradient and step 4) 2 CV, 100% step gradient, and then eluted. 1 mL of a total of 29 fractions were sequentially obtained, and each of the fractions was identified by SDS-PAGE.

TABLE 3

| Column Resin | Capto Q ImpRes |
| --- | --- |
| Column Volume | 3.6 mL |
| Binding and Washing Buffer | 50 mM sodium phosphate, pH 6.2 |
| Elution Buffer | 50 mM sodium phosphate/1M sodium chloride, pH 6.2 |

Figure 3:
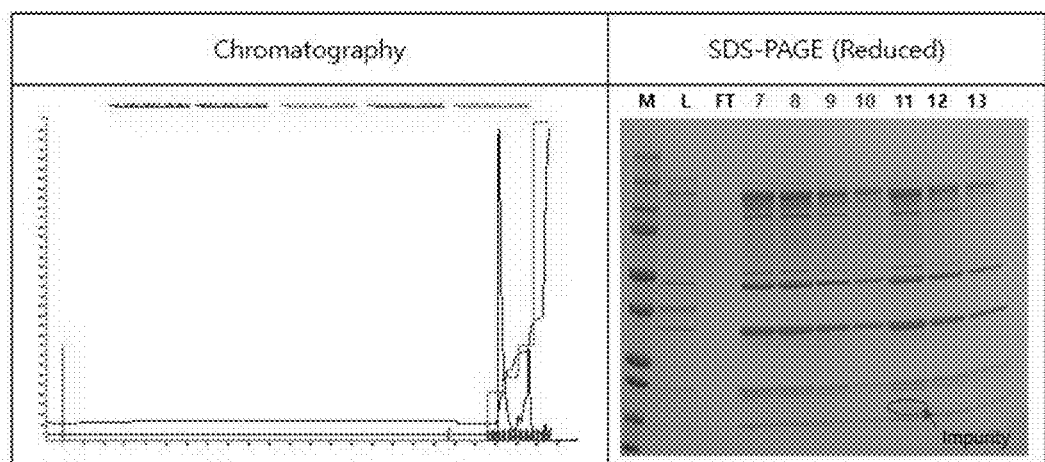
FIG. 3 shows the result of FPLC and SDS-PAGE analysis of a botulinum toxin in an eluent after anion exchange chromatography according to an embodiment of the present invention.

The results are shown in FIG. 3, and a botulinum toxin as a 900-kDa complex containing no impurities (red circles) was detected in Fractions 7 to 10 among the total of 29 fractions.

Example 3. Comparison Between Standard Product and Purified Product

Fractions 7 to 10, containing botulinum toxins purified in Example 2, and a commercially available botulinum toxin C-BoNT/A1 (Cat. No. #3102, miprolab) were each diluted to a concentration of 1 mg/ml in 50 mM sodium phosphate buffer (pH 6.2). Samples for loading were prepared under the reducing and non-reducing conditions shown in Table 4. The samples were subjected to electrophoresis in a 10-well Novex WedgeWell with 4-20% tris-glucine (Invitrogen, NP04200BOX), about 30 mL of Instant Blue stain reagent was added thereto and stained on a shaker for 60 minutes. The staining reagent was completely removed, and the sample was washed five or more times on a shaker, on which about 30 mL of purified water was put, for 30 minutes. When the background was sufficiently removed and the band could be detected, the gel was analyzed using an image analyzer.

TABLE 4

| | Reducing conditions | Non-reducing conditions |
| --- | --- | --- |
| Botulinum toxin (1 mg/ml) | 3 uL | 3 uL |
| LDS Sample Buffer (4x) | 5 uL | 5 uL |
| Sample Reducing Agent (10x) | 2 uL | 0 uL |
| Purified water | 10 uL | 12 uL |
| Total Volume | 20 uL | |

Figure 4:
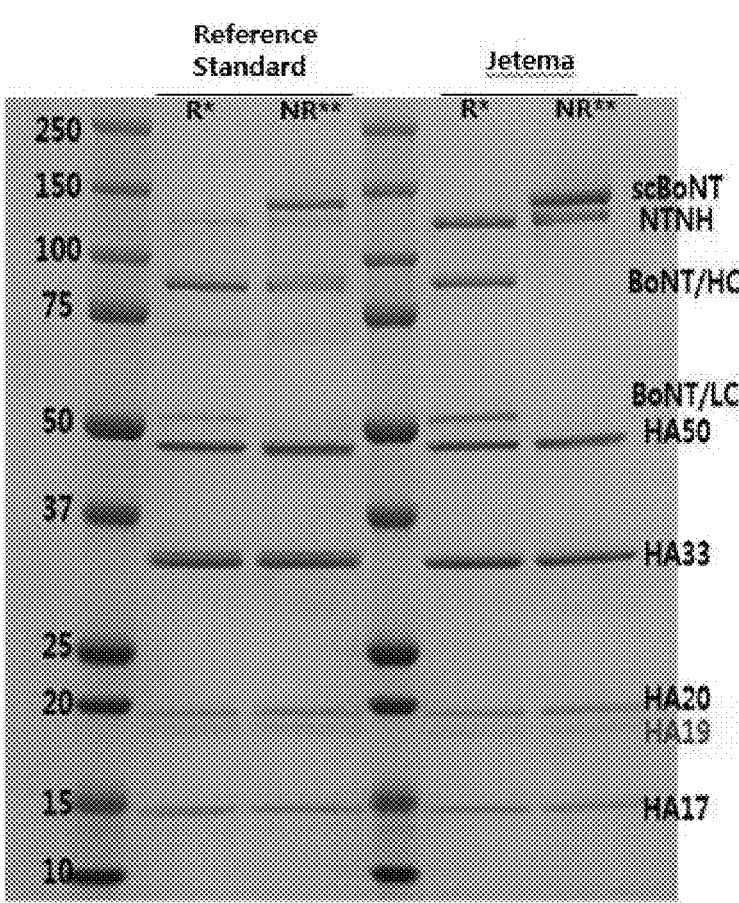
FIG. 4 shows the result of SDS-PAGE analysis to determine the purification effect of a botulinum toxin according to the present invention and a commercially available botulinum toxin.

As a result, as shown in FIG. 4, the botulinum toxin purified by the purification method of the present invention was identified in the same position as the commercially available botulinum toxin, which indicates that the purification method of the present invention can accurately purify only the target protein of interest.

Example 4. Comparison of Activity Between Standard Product and Purified Product of Botulinum Toxin of the Present Invention The activity was compared between the botulinum toxin purified in Example 2 and Botox® (Allergan Inc., 100 unit), a commercially available botulinum toxin.

Each sample was primarily diluted $2\times10^5$ to $3\times10^5$ fold, depending on the concentration thereof, and 1.45 mL of the diluted sample was diluted in 4.4 mL of physiological saline. After diluting 10 groups in the same manner as above, 0.1 mL of the sample was intraperitoneally injected into ten female ICR mice (18-22 g) in each group, and lethality was measured for 3 days. LD50 was obtained by probit statistical analysis.

The result showed that the activity of 1 ng of the botulinum toxin purified by the present invention and the botulinum toxin of Allergan Inc. were 40.73 units and 25.32 units, respectively, and the purification method according to the present invention can be performed without decreasing the activity of botulinum toxin.

Example 5. Comparison of Purity with Purification Process of Other Company

Figure 5:
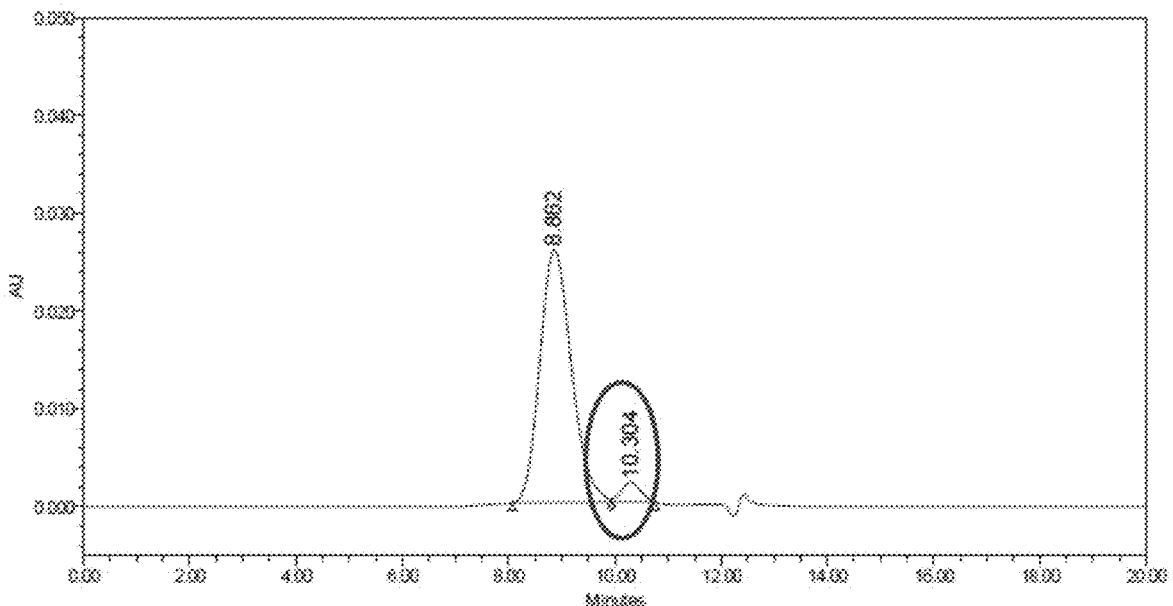
FIG. 5 shows the result of determination of the purity of the botulinum toxin purified by a purification method in accordance with Korean Patent Application No. 10-2013-0092024.

The purity of botulinum toxin, purified in accordance with the purification method described in Korean Patent Application No. 10-2013-0092024, filed by Allergan Inc., a leading manufacturer of botulinum toxin, was analyzed. As a result, as shown in FIG. 5, smaller impurities were detected in addition to the main peak, and the 900 kDa protein was not effectively separated from the 150 kDa, 300 kDa or 500 kDa protein.

Figure 6:
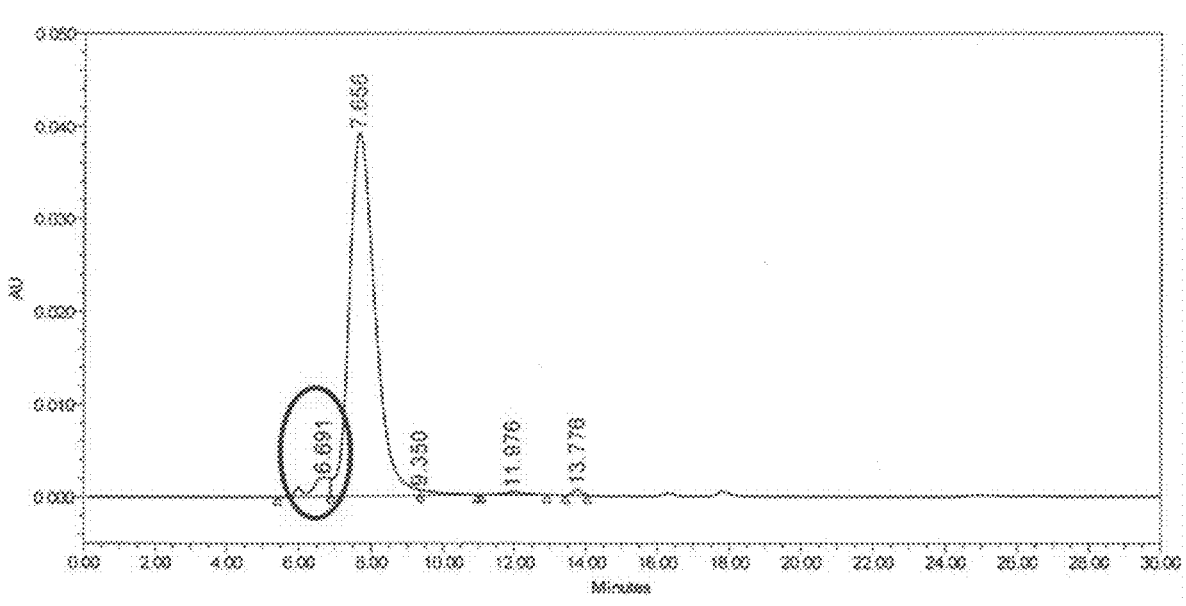
FIG. 6 shows the result of determination of the purity of the botulinum toxin purified by a purification method in accordance with U.S. patent application Ser. No. 11/932, 789.

In addition, the purity of botulinum toxin purified in accordance with the purification method of U.S. patent application Ser. No. 11/932,789, filed by Allergan Inc., was analyzed. As a result, larger impurities were detected in addition to the main peak, as shown in FIG. 6. This means that undesired precipitates were formed, and it can be expected that the purification process affected the protein structure.

Figure 7:
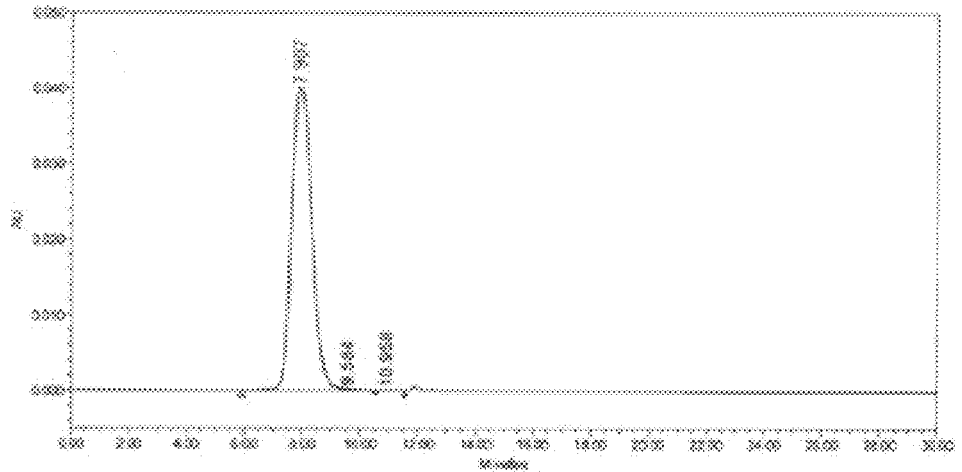
FIG. 7 shows the result of determination of the purity of the botulinum toxin purified according to the present invention.

On the other hand, as can be seen from the results of FIG. 7, the present invention enables specific purification only of toxins of about 900 kDa, and the modification of toxins during purification is also minimized.

The purity of the purified botulinum toxin was analyzed by HPLC under the conditions shown in Table 5.

TABLE 5

| Item | Condition |
| --- | --- |
| Column | PROTEIN KW-804 |
| Size | 8 mm × 300 mm |
| Stationary phase | silica gel for chromatography R (7 μm) |
| Temperature | 25° C. |
| Mobile phase | 50 mM Sodium phosphate pH 6.0, 0.15M NaCl |
| Flow rate | 1.0 mL/min |
| Running time | 30 min |
| Detection | UV detector, 278 nm |
| Injection volume | 20 μL |

Example 6. Comparison Between Three-Step
Chromatography Process of the Prior Patents and
Purification Process of Present Invention The purity and titer of purified botulinum toxin were
compared between the purification methods using the resin
used for the purification of botulinum toxin disclosed in
prior patents (US Patent Publication No. 2019-0201505 and
U.S. Pat. No. 7,452,697), and the purification methods of the
present invention using different types of resins (Table 6).
The purity was detected by HPLC in accordance with the
method of Table 5, and the titer was calculated by probit
statistical analysis using CombiStats based on the result of
the number of dead mice for 3 days in a protein concentra-
tion of 1 mg/mL using a mouse assay.

TABLE 6

| | 1$^{st}$ column resin | 2$^{nd}$ column resin | 3$^{rd}$ column resin |
|---|---|---|---|
| Present Invention (Experimental Example) | SP sepharose HP | Phenyl sepharose HP | Capto Q ImpRes |
| US 2019-0201505 (Comparative Example 1) | Butyl sepharose HP | Q sepharose HP | Phenyl sepharose HP |
| U.S. Pat. No. 7,452,697 (Comparative Example 2) | Q sepharose FF | Butyl sepharose HP | SP sepharose HP |

The types and purification conditions of the columns used
respectively in Experimental Examples and Comparative
examples are shown in Tables 7 to 8.

TABLE 7

| Comparative Example 1 (Butyl-HP → Q-HP → Phenyl-HP) | |
|---|---|
| Column | Butyl-HP (Diameter: 0.66 cm, Height: 12 cm) |
| Column volume | 4.11 mL |
| Binding & washing buffer | 50 mM Sodium Phosphate/ 2M Sodium Chloride, pH 6.2 |
| Elution buffer | 50 mM Sodium Phosphate, pH 6.2 |
| Elution condition | 2-0M Sodium Chloride 10 CV, 0M Sodium Chloride 5 CV |
| Column | Q-HP (Diameter: 0.66 cm, Height: 10 cm) |
| Column volume | 3.42 mL |
| Binding & washing buffer | 50 mM Sodium Phosphate, 6.0 |
| Elution buffer | 50 mM Sodium Phosphate/ 1M Sodium Chloride, pH 6.0 |
| Elution condition | 0.15M Sodium Chloride 3 CV, 0.20M Sodium Chloride 2 CV, 0.30M Sodium Chloride 2 CV, 1M Sodium Chloride 2 CV |
| Column | Phenyl-HP (Diameter: 0.66 cm, Height: 12 cm) |
| Column volume | 4.11 mL |
| Binding & washing buffer | 50 mM Sodium Phosphate/ 2M Sodium Chloride, pH 6.2 |
| Elution buffer | 50 mM Sodium Phosphate, pH 6.2 |
| Elution condition | 2-0M Sodium Chloride 10 CV, 0M Sodium Chloride 5 CV |

TABLE 8

| Comparative Example 2 (Q-FF(FT) → Butyl-HP → SP-HP) | |
|---|---|
| Column | Q-FF (Diameter: 2.6 cm, Height: 10 cm) |
| Column volume | 53 mL |
| Binding & washing buffer | 50 mM Sodium Phosphate, 6.0 |

TABLE 8-continued

| Comparative Example 2 (Q-FF(FT) → Butyl-HP → SP-HP) | |
|---|---|
| Elution buffer | 50 mM Sodium Phosphate/ 1M Sodium Chloride, pH 6.0 |
| Elution condition | 0.15M Sodium Chloride 3 CV, 0.20M Sodium Chloride, 2 CV, 0.30M Sodium Chloride 2 CV, Sodium Chloride 2 CV |
| Column | Butyl-HP (Diameter: 0.66 cm, Height: 12 cm) |
| Column volume | 4.11 mL |
| Binding & washing buffer | 50 mM Sodium Phosphate/ 2M Sodium Chloride, pH 6.2 |
| Elution buffer | 50 mM Sodium Phosphate, pH 6.2 |
| Elution condition | 2-0M Sodium Chloride 10 CV, 0M Sodium Chloride 5 CV |
| Column | SP-HP (Diameter: 0.66 cm, Height: 12.5 cm) |
| Column volume | 4.27 mL |
| Binding & washing buffer | 20 mM Sodium Citrate, pH 4.8 |
| Elution buffer | 20 mM Sodium Citrate/ 1M Sodium Chloride, pH 4.8 |
| Elution condition | 0-0.3M Sodium Chloride 5 CV, 1M Sodium Chloride 3 CV |

As a result, as can be seen from Table 9, the botulinum
toxin purified in accordance with Experimental Example,
which is the purification method of the present invention,
yielded a high purity of 99.4%, and the botulinum toxin
purified in accordance with Comparative Example 1 exhib-
ited lower purity and titer than in Experimental Example.
Comparative Example 2 had very lower purity and titer.
Therefore, these results showed that the botulinum toxin
purified by the method of the present invention has a
significantly higher purity and titer than those of the con-
ventional method.

TABLE 9

| | Purity (SEC-HPCL, %) | Titer (Unit/mg) |
|---|---|---|
| Present Invention (Experimental Example) | 99.4 | 4.04 × 10$^7$ |
| US 2019-0201505 (Comparative Example 1) | 93.3 | 3.78 × 10$^7$ |
| U.S. Pat. No. 7,452,697 (Comparative Example 2) | 45.2 | Less than 1.0 × 10$^7$ |

Although specific configurations of the present invention
have been described in detail, those skilled in the art will
appreciate that this description is provided to set forth
preferred embodiments for illustrative purposes and should
not be construed as limiting the scope of the present inven-
tion. Therefore, the substantial scope of the present inven-
tion is defined by the accompanying claims and equivalents
thereto.

What is claimed is:

1. A method of purifying a 900 kDa botulinum toxin
complex, comprising:
(a) pre-treating a culture solution containing a botulinum
toxin;
(b) applying the pre-treated botulinum toxin from step (a)
to cation exchange chromatography using an SP col-
umn to bind the botulinum toxin to the cation exchange
chromatography medium, and separating the botulinum
toxin which is bound to the cation exchange chroma-
tography medium, to obtain a botulinum toxin-contain-
ing solution;

(c) applying the botulinum toxin-containing solution obtained in step (b) to hydrophobic chromatography using a phenyl column to obtain a botulinum toxin-containing solution; and (d) applying the botulinum toxin-containing solution obtained in step (c) to anion exchange chromatography using a Q column to bind the botulinum toxin to the anion exchange chromatography medium, and separating the 900 kDa botulinum toxin complex which is bound to the anion exchange chromatography medium, to purify the botulinum toxin, wherein the SP column is selected from the group consisting of (i) a column containing a resin containing a sulfopropyl functional group, having a 6% spherical, cross-linked agarose matrix form, and having a DBC of 55 mg/mL based on ribonuclease A and a particle size of 34 μm, (ii) an SP FF (fast flow) column, and (iii) a column containing a cation exchange resin comprising an agarose matrix and a sulfonate cation exchanger coupled to the agarose matrix;

wherein the phenyl column is selected from the group consisting of (i) a column containing a resin having a cross-linked agarose 6% matrix form, a degree of substitution of 25 μmol phenyl groups/mL, and a bead size of 34 μm, (ii) a phenyl FF (Fast Flow) column, and (iii) a column containing a hydrophobic chromatography resin comprising a cross-linked agarose matrix and phenyl group ligands; and wherein the Q column is selected from the group consisting of (i) a column containing an anion resin comprising an agarose matrix and quaternary amine functional groups $CH_2CH_2CH_2SO_3$, (ii) a column containing a resin containing a methacrylic bead with a particle size of 65 μm comprising a quaternary ammonium (Q) functional group, (iii) a Q FF column, and a Q HP column.

2. The method according to claim 1, wherein the botulinum toxin in step (b) is dissolved in a 10 to 30 mM sodium citrate buffer having a pH of 4.5 to 5.5 and is then injected into the SP column.

3. The method according to claim 1, wherein the botulinum toxin in step (b) is eluted with a 30 to 70 mM sodium citrate buffer having a pH of 4.5 to 5.5 supplemented with 0.5 to 1.5M sodium chloride.

4. The method according to claim 1, wherein the botulinum toxin in step (c) is dissolved in a 30 to 70 mM sodium phosphate buffer having a pH of 5.7 to 6.7 supplemented with 1.8 to 2.2M sodium chloride and then injected into the phenyl column.

5. The method according to claim 1, wherein the botulinum toxin in step (c) is eluted with a 30 to 70 mM sodium phosphate buffer having a pH of 5.7 to 6.7.

6. The method according to claim 1, wherein the botulinum toxin in step (d) is dissolved in a 40 to 60 mM sodium phosphate buffer having a pH of 5.7 to 6.7 and then injected into the Q column.

7. The method according to claim 1, wherein the botulinum toxin in step (d) is eluted with a 40 to 60 mM sodium phosphate buffer having a pH of 5.7 to 6.7 supplemented with 0.8 to 1.2M sodium chloride.

8. The method according to claim 1, wherein the purified botulinum toxin is botulinum toxin A having a purity of 99% or more.

* * * * *